(12) United States Patent
Li et al.

(10) Patent No.: US 9,353,410 B2
(45) Date of Patent: May 31, 2016

(54) MICRO-REACTOR DEVICE

(71) Applicants: CapitalBio Corporation, Beijing (CN); Tsinghua University, Beijing (CN)

(72) Inventors: Hang Li, Beijing (CN); Jinglin Zhou, Beijing (CN); Dong Wang, Beijing (CN)

(73) Assignees: CapitalBio Corporation, Beijing (CN); Tsinghua University, Beijing (CN)

( * ) Notice: Subject to any disclaimer, the term of this patent is extended or adjusted under 35 U.S.C. 154(b) by 0 days.

(21) Appl. No.: 14/340,368

(22) Filed: Jul. 24, 2014

(65) Prior Publication Data

US 2015/0031037 A1 Jan. 29, 2015

(30) Foreign Application Priority Data

Jul. 25, 2013 (CN) .......................... 2013 1 0316309

(51) Int. Cl.
| | |
|---|---|
| *G01N 35/04* | (2006.01) |
| *C12Q 1/68* | (2006.01) |
| *G01N 35/00* | (2006.01) |
| *G01N 27/74* | (2006.01) |
| *B03C 1/06* | (2006.01) |

(52) U.S. Cl.
CPC .............. *C12Q 1/686* (2013.01); *G01N 27/745* (2013.01); *G01N 35/0098* (2013.01); *B03C 1/06* (2013.01)

(58) Field of Classification Search
CPC .................................................. G01N 35/0098
See application file for complete search history.

(56) References Cited

U.S. PATENT DOCUMENTS

| | | | |
|---|---|---|---|
| 5,807,527 A | 9/1998 | Burgoyne | |
| 6,168,922 B1 | 1/2001 | Harvey et al. | |
| RE37,891 E | 10/2002 | Collins et al. | |
| 2010/0248981 A1* | 9/2010 | Shirazi | ................... B01L 9/523 506/9 |
| 2012/0329124 A1* | 12/2012 | Tajima | ................... B03C 1/015 435/176 |

FOREIGN PATENT DOCUMENTS

| | | | |
|---|---|---|---|
| CN | 2890059 | 4/2007 | |
| CN | 103394410 | 11/2013 | |
| WO | WO 2011059076 A1 * | 5/2011 | .............. B03C 1/015 |

* cited by examiner

*Primary Examiner* — P. Kathryn Wright
(74) *Attorney, Agent, or Firm* — Morrison & Foerster LLP (57) ABSTRACT

In some aspects, the present disclosure provides a magnetic rack comprising a lateral movement structure and/or a longitudinal movement structure. In particular embodiments, the lateral movement structure and/or longitudinal movement structure move one or more magnets to or away from a reaction tube, in order to control the magnetic forces exerted on microbeads in the reaction tube. The microbeads are attracted onto the reaction tube wall, thereby facilitating separation of the microbeads from a solution in the tube. In particular embodiments, the magnetic rack is used to extract or purify nucleic acid from a sample.

21 Claims, 1 Drawing Sheet

MICRO-REACTOR DEVICE

CROSS-REFERENCE TO RELATED APPLICATIONS

This application claims priority from Chinese Patent Application No. 201310316309.7, filed Jul. 25, 2013, published as CN 103394410 A, published Nov. 20, 2013, the disclosures of which are incorporated herein by reference in their entireties for all purposes.

TECHNICAL FIELD

The present disclosure generally relates to the field of devices and methods based on magnetic interactions, for example, for the processing of a biological sample or for performing a biological reaction. In particular aspects, a magnetic rack is disclosed for separating microbeads from a liquid sample. Devices and methods for batch processing of samples are provided. In particular embodiments, the devices and methods are automated for nucleic acid extraction and/or purification.

BACKGROUND

In the following discussion, certain articles and methods are described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

Nucleic acid-based genetic methods for identification of cells and microorganisms have greatly reduced the time and labor involved in clinical diagnosis. Such methods include, for example, nucleic acid hybridization (e.g., Southerns/microarrays and slot blots), nucleotide sequencing, nucleic acid cloning techniques, restriction digestion of nucleic acids and nucleic acid amplification. In particular, nucleic acid amplification has provided means for rapid, sensitive and specific identification of cells or viruses by amplification and detection of specific genes or gene fragments. Standard techniques for detection of specific nucleotide sequences generally employ nucleic acids that have been purified away from cellular proteins and other cellular contaminants.

With the development of molecular biology, the number of samples that need to be handled by clinical diagnosis and biological experiments is also growing rapidly. Automated sample processing and reaction equipment has been developed and is widely used, for example, for extracting nucleic acids from clinical samples. Automated methods that use beads to extract nucleic acid are maturing, and have seen increasingly widespread application. Existing devices for this purpose typically require various steps such as bead collection, bead release, and bead transfer. The present disclosure addresses some of the issues with existing methods and devices.

SUMMARY

The summary is not intended to be used to limit the scope of the claimed subject matter. Other features, details, utilities, and advantages of the claimed subject matter will be apparent from the detailed description including those aspects disclosed in the accompanying drawings and in the appended claims.

In one aspect, a magnetic rack comprising a longitudinal movement structure is disclosed. In some embodiments, the longitudinal movement structure comprises a motor mounting plate; a lifting motor; a motion platform; and a magnet holder on the motion platform, which magnet holder is configured to hold one or more magnets. In one aspect, the lifting motor is configured to move the motion platform in a direction substantially perpendicular to the motor mounting plate and/or the motion platform.

In another aspect, disclosed herein is a magnetic rack comprising a lateral movement structure. In some embodiments, the lateral movement structure comprises: a motion platform; a driving wheel and a driven wheel on the motion platform; a timing belt engaging both the driving wheel and the driven wheel; and a magnet holder engaging the timing belt, which magnet holder is configured to hold one or more magnets. In some aspects, the timing belt is configured to be actuated by the driving wheel and to move the magnet holder laterally along a path on the motion platform.

In yet another aspect, the present disclosure provides a magnetic rack comprising a lateral movement structure and a longitudinal movement structure. In one embodiment, the lateral movement structure comprises: a motion platform; a driving wheel and a driven wheel on the motion platform; a timing belt engaging both the driving wheel and the driven wheel; and a magnet holder engaging the timing belt, which magnet holder is configured to hold one or more magnets; and the longitudinal movement structure comprises a lifting motor. In one aspect, the timing belt is configured to be actuated by the driving wheel and to move the magnet holder laterally along a path on the motion platform. In another aspect, the lifting motor is configured to move the motion platform in a direction substantially perpendicular to the motion platform.

In any of the preceding embodiments, the lateral movement structure can further comprise a linear guide on the motion platform, and the magnet holder is connected to or engages the linear guide. In one aspect, the timing belt is configured to move the magnet holder laterally along the linear guide.

In any of the preceding embodiments, the magnetic rack can further comprise a lifting guide bushing and a lifting guide column. In one aspect, the lifting guide bushing is connected to or engages the motion platform. In another aspect, the lifting guide bushing and the lifting guide column are configured to engage each other to form a lifting structure. In one aspect, the lifting motor is configured to actuate the lifting structure to move the motion platform in a direction substantially perpendicular to the motion platform.

In any of the preceding embodiments, the magnetic rack can further comprise a photoelectric block or photoelectric block element on the motion platform. In any of the preceding embodiments, the longitudinal movement structure can further comprise a motor mounting plate. In one aspect, the lifting motor is mounted on the motor mounting plate. In another aspect, the motor mounting plate comprises a photoelectric sensor.

In any of the preceding embodiments, the magnetic rack can further comprise a photoelectric block or photoelectric block element on the magnet holder and/or a photoelectric limit element on the motion platform.

In any of the preceding embodiments, the magnetic rack can further comprise a fixing belt plate on the timing belt. In one aspect, the fixing belt plate and the magnet holder are connected or engage each other. In another aspect, the timing belt actuates the lateral movement of the magnet holder via the fixing belt plate fixed on the timing belt.

In any of the preceding embodiments, the magnetic rack can further comprise a mounting seat and a tray for receiving one or more reaction tubes or plates. In one aspect, the tray is configured to be placed on or in the mounting seat. In one aspect, the mounting seat houses the lateral movement structure and/or the longitudinal movement structure.

In any of the preceding embodiments, the magnetic rack can further comprise a driven wheel bearing and a driven wheel bearing housing. In one aspect, the driven wheel and the driven wheel bearing are connected or engage with each other. In another aspect, the driven wheel bearing and the driven wheel bearing housing are connected or engage with each other. In yet another aspect, the driven wheel bearing housing is on the motion platform.

In one embodiment, provided herein is a method of performing a magnetic bead-based process. In one aspect, the method comprises placing a receptacle on a magnetic rack comprising a longitudinal movement structure as disclosed herein, which receptacle contains a sample with one or more magnetic beads. In another aspect, the method further comprises actuating the lifting motor to move the motion platform comprising one or more magnets in the magnet holder in a direction substantially perpendicular to the motion platform, such that the one or more magnets in the magnet holder are moved toward the receptacle to attract or adsorb the one or more magnetic beads onto the wall of the receptacle. In one aspect, the method further comprises removing or adding a reagent or solution into the receptacle, and the one or more magnetic beads remain adsorbed on the wall of the receptacle when the reagent or solution is being removed or added. In one embodiment, the wall of the receptacle is a side wall. In one aspect, the method further comprises a step between the actuating step and the removing or adding step, and the step comprises actuating the lifting motor to move the motion platform in a direction substantially perpendicular to the motion platform. In one aspect, the one or more magnets are moved toward the bottom of the receptacle to attract or adsorb the magnetic bead onto the bottom of the receptacle.

In one embodiment, provided herein is a method of performing a magnetic bead-based process, and the method comprises placing a receptacle on a magnetic rack comprising a lateral movement structure as disclosed herein. In one aspect, the receptacle contains a sample with a magnetic bead. In one aspect, the method further comprises actuating the driving wheel to move the magnet holder holding one or more magnets laterally along a path on the motion platform. In one embodiment, the one or more magnets are moved toward the receptacle to attract or adsorb the magnetic bead onto the wall of the receptacle. The method can further comprise removing or adding a reagent or solution into the receptacle. In one aspect, the magnetic bead remains adsorbed on the wall of the receptacle when the reagent or solution is being removed or added. In one aspect, the wall of the receptacle is a side wall.

In one embodiment, provided herein is a method of performing a magnetic bead-based process. The method comprises placing a receptacle on a magnetic rack comprising a lateral movement structure and a longitudinal movement structure as disclosed herein. In one aspect, the receptacle contains a sample with a magnetic bead. In one aspect, the method further comprises actuating the lifting motor of the longitudinal movement structure to move the motion platform comprising one or more magnets in the magnet holder in a direction substantially perpendicular to the motion platform. In one aspect, the one or more magnets are moved toward the receptacle to attract or adsorb the magnetic bead onto a side wall of the receptacle. The method can further comprise actuating the driving wheel of the lateral movement structure to move the magnet holder laterally along a path on the motion platform. In one aspect, the one or more magnets are moved toward the bottom of the receptacle to attract or adsorb the magnetic bead from the side wall onto the bottom of the receptacle.

In one aspect, the above method can further comprise a step of removing or adding a reagent or solution into the receptacle (the magnetic bead remains adsorbed on the side wall of the receptacle when the reagent or solution is being removed or added), and/or a step of removing or adding a reagent or solution into the receptacle (the magnetic bead remains adsorbed on the bottom of the receptacle when the reagent or solution is being removed or added). In other aspects, the above methods can further comprise a step of actuating the lifting motor to move the motion platform substantially perpendicular to the motion platform, such that the one or more magnets are moved away from the receptacle to release the magnetic bead from the side wall of the receptacle; and/or a step of actuating the driving wheel to move the magnet holder laterally on the motion platform, such that the one or more magnets are moved away from the receptacle to release the magnetic bead from the bottom of the receptacle.

BRIEF DESCRIPTION OF THE DRAWINGS

FIG. 1 is an exploded view of a device disclosed herein. The mounting seat (1), tube tray (2), motor mounting plate (3), lifting motor (4), photoelectric sensor (5) (shown as a U-typed electro-optical (EO) sensor), motion platform (6), lifting guide column (7), lifting guide bushing (8), photoelectric block column (9), drive wheel motor (10), driving wheel (11), driven wheel (12), driven wheel bearing housing (13), timing belt (14), linear guide (15), magnet holders (16), fixing belt plate (17), photoelectric sheet (18), home photoelectric device (19), magnets (20), and test plate (21) (shown as a PCR microplate) are shown.

DETAILED DESCRIPTION

A detailed description of one or more embodiments of the claimed subject matter is provided below along with accompanying figures that illustrate the principles of the claimed subject matter. The claimed subject matter is described in connection with such embodiments, but is not limited to any particular embodiment. It is to be understood that the claimed subject matter may be embodied in various forms, and encompasses numerous alternatives, modifications and equivalents. Therefore, specific details disclosed herein are not to be interpreted as limiting, but rather as a basis for the claims and as a representative basis for teaching one skilled in the art to employ the claimed subject matter in virtually any appropriately detailed system, structure, or manner. Numerous specific details are set forth in the following description in order to provide a thorough understanding of the present disclosure. These details are provided for the purpose of example and the claimed subject matter may be practiced according to the claims without some or all of these specific details. It is to be understood that other embodiments can be used and structural changes can be made without departing from the scope of the claimed subject matter. It should be understood that the various features and functionality described in one or more of the individual embodiments are not limited in their applicability to the particular embodiment with which they are described. They instead can, be applied, alone or in some combination, to one or more of the other embodiments of the disclosure, whether or not such embodiments are described, and whether or not such features are presented as being a part of a described embodiment. For the purpose of clarity, technical material that is known in the technical fields related to the claimed subject matter has not been described in detail so that the claimed subject matter is not unnecessarily obscured.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

All publications, including patent documents and scientific articles, referred to in this application are incorporated by reference in their entireties for all purposes to the same extent as if each individual publication were individually incorporated by reference. If a definition set forth herein is contrary to or otherwise inconsistent with a definition set forth in the patents, patent applications, published applications or other publications that are herein incorporated by reference, the definition set forth herein prevails over the definition that is incorporated herein by reference. Citation of the publications or documents is not intended as an admission that any of them is pertinent prior art, nor does it constitute any admission as to the contents or date of these publications or documents.

All headings are for the convenience of the reader and should not be used to limit the meaning of the text that follows the heading, unless so specified.

As used herein and in the appended claims, the singular forms "a," "an," and "the" include plural referents unless the context clearly dictates otherwise. For example, "a" or "an" means "at least one" or "one or more." Thus, reference to "a magnet" refers to one or more magnets, and reference to "the method" includes reference to equivalent steps and methods disclosed herein and/or known to those skilled in the art, and so forth.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

In one embodiment, the magnetic forces between magnetic beads in a reaction tube and a corresponding magnet in the magnetic rack are substantially identical among samples processed in the same batch. As used herein, "substantially identical" magnetic forces mean that the differences among the magnetic forces are sufficiently small not to statistically affect assay uniformity. Normally, the difference between the largest magnetic force and the smallest magnetic force is less than about 50% of the largest magnetic force. Preferably, the difference between the largest magnetic force and the smallest magnetic force is less than about 40%, about 30%, about 20%, about 10%, about 5%, about 2%, about 1%, about 0.5%, about 0.1%, about 0.01%, or less than about 0.001% of the largest magnetic force.

In one embodiment, the lifting motor is configured to move the motion platform in a direction substantially perpendicular to the motor mounting plate and/or the motion platform. As used herein, "substantially perpendicular" means that the angle between the direction of the movement of the lifting motor and the motor mounting plate and/or the motion platform is at least more than 45 degrees or less than 135 degrees. In some specific embodiments, the angle is at about 50, 55, 60, 65, 70, 75, 80, 85, 86, 87, 88, 89, or 90 degrees. In other specific embodiments, the angle is at about 130, 125, 120, 115, 110, 105, 100, 95, 94, 93, 92, or 91 degrees.

In some embodiments, the magnet holder moves the magnets in a direction substantially parallel to the surface of the motion platform of the lateral movement structure. As used herein, "substantially parallel" means that the angle between the direction of the magnet/magnet holder movement and the surface of the motion platform is at least less than 45 degrees or more than 135 degrees. In some specific embodiments, the angle is at about 40, 35, 30, 25, 20, 15, 10, 5, 4, 3, 2, 1, or 0 degree. In other specific embodiments, the angle is at about 140, 145, 150, 155, 160, 165, 170, 175, 176, 177, 178, 179, or 180 degrees.

In one embodiment, when the microbeads are attracted onto the wall or bottom of a reaction tube and the liquid in the tube is aspired, the aspired liquid is substantially free of the beads and/or molecules, complexes, viral particles, organelles, cellular components, or cells coupled to the beads. As used herein, the term "substantially free" means that the aspired liquid contains less than 30%, preferably less than 20%, preferably less than 10%, preferably less than 5%, preferably less than 2%, preferably less than 1%, preferably less than 0.5%, preferably less than 0.1%, preferably less than 0.01%, more preferably less than 0.001%, even more preferably less than 0.0001%, most preferably zero percent of the beads and/or molecules and complexes bound thereto by weight of the aspired liquid.

As used herein, a "biological sample" includes any sample obtained from a living or viral (or prion) source or other source of macromolecules and biomolecules, and includes any cell type or tissue of a subject from which nucleic acid, protein and/or other macromolecule can be obtained. The biological sample can be a sample obtained directly from a biological source or a sample that is processed. For example, isolated nucleic acids that are amplified constitute a biological sample.

Biological samples include, but are not limited to, body fluids, such as blood, plasma, serum, cerebrospinal fluid, synovial fluid, urine and sweat, tissue and organ samples from animals and plants and processed samples derived therefrom. In particular embodiments, a biological sample is processed using a magnetic rack disclosed herein, for example, for extracting and/or purifying nucleic acid from the biological sample.

As used herein, a "composition" can be any mixture of two or more products or compounds. It may be a solution, a suspension, liquid, powder, a paste, aqueous, non-aqueous or any combination thereof. A biological sample of the present disclosure encompasses a sample in the form of a solution, a suspension, a liquid, a powder, a paste, an aqueous sample, or a non-aqueous sample.

In one embodiment, the magnetic rack is used to extract or purify naturally occurring or synthetic nucleic acid from one or more samples. The terms "polynucleotide," "oligonucleotide," "nucleic acid" and "nucleic acid molecule" are used interchangeably herein to refer to a polymeric form of nucleotides of any length, and comprise ribonucleotides, deoxyribonucleotides, and analogs or mixtures thereof. The terms include triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide.

More particularly, the terms "polynucleotide," "oligonucleotide," "nucleic acid," and "nucleic acid molecule" include polydeoxyribonucleotides (containing 2-deoxy-D-ribose), polyribonucleotides (containing D-ribose), including tRNA, rRNA, hRNA, and mRNA, whether spliced or unspliced, any other type of polynucleotide which is an N- or C-glycoside of a purine or pyrimidine base, and other polymers containing nonnucleotidic backbones, for example, polyamide (e.g., peptide nucleic acids ("PNAs")) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. Thus, these terms include, for example, 3'-deoxy-2',5'-DNA, oligodeoxyribonucleotide N3' to P5' phosphoramidates, 2'-O-alkyl-substituted RNA, hybrids between DNA and RNA or between PNAs and DNA or RNA, and also include known types of modifications, for example, labels, alkylation, "caps," substitution of one or more of the nucleotides with an analog, inter-nucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalkylphosphoramidates, aminoalkylphosphotriesters), those containing pendant moieties, such as, for example, proteins (including enzymes (e.g. nucleases), toxins, antibodies, signal peptides, poly-L-lysine, etc.), those with intercalators (e.g., acridine, psoralen, etc.), those containing chelates (of, e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide. A nucleic acid generally will contain phosphodiester bonds, although in some cases nucleic acid analogs may be included that have alternative backbones such as phosphoramidite, phosphorodithioate, or methylphosphoroamidite linkages; or peptide nucleic acid backbones and linkages. Other analog nucleic acids include those with bicyclic structures including locked nucleic acids, positive backbones, non-ionic backbones and non-ribose backbones. Modifications of the ribose-phosphate backbone may be done to increase the stability of the molecules; for example, PNA: DNA hybrids can exhibit higher stability in some environments. The terms "polynucleotide," "oligonucleotide," "nucleic acid" and "nucleic acid molecule" can comprise any suitable length, such as at least 5, 6, 7, 8, 9, 10, 20, 30, 40, 50, 100, 200, 300, 400, 500, 1,000 or more nucleotides.

The terms "polypeptide," "oligopeptide," "peptide," and "protein" are used interchangeably herein to refer to polymers of amino acids of any length, e.g., at least 5, 6, 7, 8, 9, 10, 20, 30, 40, 50, 100, 200, 300, 400, 500, 1,000 or more amino acids. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. In particular embodiments, a polypeptide or protein can be coupled to microbeads. In some aspects, a sample containing a target polypeptide or protein can be processed using a magnetic rack disclosed herein. For example, the polypeptide or protein can be extracted or purified from the sample, using a bead coupled to a binding agent (e.g., an antibody) specific to the polypeptide or protein in order to capture the target molecule. The bead can then be separated from the sample (e.g., a liquid or a solution), washed, and/or subjected to further treatment, before the target polypeptide or protein is released from the bead.

The terms "binder," "binding agent," "binding moiety," and "binding group" as used herein refer to any agent or any moiety or group thereof that specifically binds to a molecule of interest, e.g., a biological molecule or portions or complexes thereof with other molecules.

A target that can be extracted, purified, detected, and/or analyzed using the device disclosed herein can be any biological molecules including but not limited to proteins, nucleic acids, lipids, carbohydrates, ions, or multicomponent complexes containing any of the above. Examples of subcellular targets include organelles, e.g., mitochondria, Golgi apparatus, endoplasmic reticulum, chloroplasts, endocytic vesicles, exocytic vesicles, vacuoles, lysosomes, etc. Exemplary nucleic acid target can include genomic DNA of various conformations (e.g., A-DNA, B-DNA, Z-DNA), mitochondria DNA (mtDNA), mRNA, tRNA, rRNA, hRNA, miRNA, and piRNA.

As used herein, the term "binding" refers to an attractive interaction between two molecules which results in a stable association in which the molecules are in close proximity to each other. Molecular binding can be classified into the following types: non-covalent, reversible covalent and irreversible covalent. Molecules that can participate in molecular binding include proteins, nucleic acids, carbohydrates, lipids, and small organic molecules such as pharmaceutical compounds. For example, proteins that form stable complexes with other molecules are often referred to as receptors while their binding partners are called ligands. Nucleic acids can also form stable complex with themselves or others, for example, DNA-protein complex, DNA-DNA complex, DNA-RNA complex.

As used herein, the term "specific binding" refers to the specificity of a binder, e.g., an antibody, such that it preferentially binds to a target, such as a polypeptide antigen. When referring to a binding partner, e.g., protein, nucleic acid, antibody or other affinity capture agent, etc., "specific binding" can include a binding reaction of two or more binding partners with high affinity and/or complementarity to ensure selective hybridization under designated assay conditions. Typically, specific binding will be at least three times the standard deviation of the background signal. Thus, under designated conditions the binding partner binds to its particular target molecule and does not bind in a significant amount to other molecules present in the sample. Recognition by a binder or an antibody of a particular target in the presence of other potential interfering substances is one characteristic of such binding. Preferably, binders, antibodies or antibody fragments that are specific for or bind specifically to a target bind to the target with higher affinity than binding to other non-target substances. Also preferably, binders, antibodies or antibody fragments that are specific for or bind specifically to a target avoid binding to a significant percentage of non-target substances, e.g., non-target substances present in a testing sample. In some embodiments, binders, antibodies or antibody fragments of the present disclosure avoid binding greater than about 90% of non-target substances, although higher percentages are clearly contemplated and preferred. For example, binders, antibodies or antibody fragments of the present disclosure avoid binding about 91%, about 92%, about 93%, about 94%, about 95%, about 96%, about 97%, about 98%, about 99%, and about 99% or more of non-target substances. In other embodiments, binders, antibodies or antibody fragments of the present disclosure avoid binding greater than about 10%, 20%, 30%, 40%, 50%, 60%, or 70%, or greater than about 75%, or greater than about 80%, or greater than about 85% of non-target substances.

A variety of assays or reactions can be performed using a magnetic rack disclosed herein. Examples include and are not limited to hybridization, nucleic acid amplification, PCR, ligation, nucleic acid synthesis, and sequence determination (such as nucleic acid or amino acid sequencing).

"Hybridization" as used herein may refer to the process in which two single-stranded polynucleotides bind non-covalently to form a stable double-stranded polynucleotide. In one aspect, the resulting double-stranded polynucleotide can be a "hybrid" or "duplex." "Hybridization conditions" typically include salt concentrations of approximately less than 1 M, often less than about 500 mM and may be less than about 200 mM. Hybridizations are often performed under stringent conditions, i.e., conditions under which a sequence will hybridize to its target sequence but will not hybridize to other, non-complementary sequences. Stringent conditions are sequence-dependent and are different in different circumstances. Suitable moderate stringency and high stringency hybridization buffers and conditions are well known to those of skill in the art and are described, for example, in Sambrook et al., Molecular Cloning: A Laboratory Manual, 2nd ed., Cold Spring Harbor Press, Plainview, N.Y. (1989); and Ausubel et al., Short Protocols in Molecular Biology, 4th ed., John Wiley & Sons (1999).

"Ligation" may refer to the formation of a covalent bond or linkage between the termini of two or more nucleic acids, e.g., oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon terminal nucleotide of one oligonucleotide with a 3' carbon of another nucleotide.

"Sequence determination" and the like include determination of information relating to the nucleotide base sequence of a nucleic acid. Such information may include the identification or determination of partial as well as full sequence information of the nucleic acid. Sequence information may be determined with varying degrees of statistical reliability or confidence. In one aspect, the term includes the determination of the identity and ordering of a plurality of contiguous nucleotides in a nucleic acid. "High throughput sequencing" or "next generation sequencing" includes sequence determination using methods that determine many (typically thousands to billions) of nucleic acid sequences in an intrinsically parallel manner, i.e. where DNA templates are prepared for sequencing not one at a time, but in a bulk process, and where many sequences are read out preferably in parallel, or alternatively using an ultra-high throughput serial process that itself may be parallelized. Such methods include but are not limited to pyrosequencing (for example, as commercialized by 454 Life Sciences, Inc., Branford, Conn.); sequencing by ligation (for example, as commercialized in the SOLiD™ technology, Life Technologies, Inc., Carlsbad, Calif.); sequencing by synthesis using modified nucleotides (such as commercialized in TruSeq™ and HiSeq™ technology by Illumina, Inc., San Diego, Calif.; HeliScope™ by Helicos Biosciences Corporation, Cambridge, Mass.; and PacBio RS by Pacific Biosciences of California, Inc., Menlo Park, Calif.), sequencing by ion detection technologies (such as Ion Torrent™ technology, Life Technologies, Carlsbad, Calif.); sequencing of DNA nanoballs (Complete Genomics, Inc., Mountain View, Calif.); nanopore-based sequencing technologies (for example, as developed by Oxford Nanopore Technologies, LTD, Oxford, UK), and like highly parallelized sequencing methods. In certain embodiments, a magnetic rack disclosed herein is compatible with a sequencing technology, in particular, a nucleic acid sequencing technology. Due to the flexibility that the presently disclosed method offers, the present magnetic rack can be adapted or modified to be compatible with a nucleic acid sequencing technology.

Standard techniques for detection of specific nucleotide sequences generally employ nucleic acids that have been extracted or purified away from cellular proteins and other cellular contaminants. Nucleic acid extraction or purification methods based on magnetic beads have been developed and widely used. These methods typically require various steps such as bead collection, bead release, and bead transfer.

Currently, two major categories of methods exist for separating magnetic beads in a sample. The first one relies on the relative movement between a magnet and a magnetic coat to achieve the collection, release, and/or transfer of beads, for the purpose of performing nucleic acid extraction. For example, Chinese Patent No. CN2890059 Y (Applicant No. 200620054569.7) discloses a method in this category. The method requires the use of a matching kit and the transfer of beads, and requires the use of a magnetic coat for isolating the magnet and the reagents. The magnetic coat is a disposable supply. In this method, the apparatus and the matching kit constitute a closed system, and are thus not easily adapted or modified.

The other category of methods use tips for pipetting or shaking to mix beads. A plate gripper is used to transfer plates to a magnetic rack or frame to adsorb beads. After that, pipette tips are used to transfer liquid to achieve nucleic acid extraction. This method has been widely used in automatic liquid workstations that are currently available on the market.

In the above methods and devices, the suitability of the magnetic rack for different beads is typically controlled by adsorption time, and the methods and devices are often not amiable to modifications or adaptations. In addition, the pipetting step, liquid transferring step, and bead adsorbing step are often not synchronized or coordinated among samples. In certain aspects, the present disclosure addresses these issues.

Magnetic Rack for Reaction and/or Sample Processing

In one aspect, the present disclosure provides a magnetic rack (e.g., a magnetic separation rack, for separating a target molecule or complex from a mixture), and a device comprising the magnetic rack. In one embodiment, the magnetic rack is used for batch processing of reaction plates and/or tubes, such as 96-well plates and PCR microplates. In one aspect, the magnetic rack or device is adjustable in position, for example, the position of a magnet in the magnetic rack relative to a reaction tube can be adjusted. In one aspect, magnetic beads are included in a reaction (e.g., a biological reaction such as a PCR reaction, an enzyme based reaction, or a diagnostic test), and a magnetic rack disclosed herein is used to attract the magnetic beads which are coupled to one or more reaction reagents or products, thereby separating the reaction reagent(s) or product(s) from the rest of the reaction mixture. In one aspect, the magnetic rack allows various reactions of a biological or chemical process to be conducted at the same location, for example, in the same reaction receptacle (e.g., a reaction tube or a reaction well on a plate). In certain aspects, this can eliminate the need of transferring materials between reaction receptacles, which could save time and increase the success rate and/or reproducibility of a reaction. In other aspects, the present disclosure provides intelligent control of magnetic forces to meet the needs of different systems, for example, by using a supporting program to auto-regulate the magnetic force exerted on the magnetic beads.

In a first embodiment, provided herein is a magnetic rack, characterized in that it comprises a lateral movement structure, wherein the lateral movement structure comprises a motion platform, and a driving wheel and a driven wheel at about each end of the motion platform; wherein the driving wheel and the driven wheel engage with each other or are connected; wherein the driving wheel and the driven wheel both engage a common timing belt; wherein the motion platform comprises a linear guide, a magnet holder connected to or engaged with the linear guide, and at least one magnet on the magnet holder; wherein the magnet holder and the timing belt are connected or engaged.

In a second embodiment, provided herein is a magnetic rack, characterized in that it comprises a longitudinal movement structure, wherein the longitudinal movement structure comprises: a motor mounting plate; a lifting motor fixed on the motor mounting plate; a motion platform; a magnet holder on the motion platform; and at least one magnet on the magnet holder, wherein the lifting motor is configured to actuate the movement of the motion platform in a direction substantially perpendicular to the motor mounting plate and/or to the motion platform.

In a third embodiment, provided herein is a magnetic rack, characterized in that it comprises a lateral movement structure and a longitudinal movement structure, wherein the lateral movement structure comprises: a motion platform; and a driving wheel and a driven wheel at about each end of the motion platform, wherein the driving wheel and the driven wheel are connected or engaged with each other, wherein the driving wheel and the driven wheel are both engaged with a timing belt, wherein the motion platform comprises a linear guide, a magnet holder connected or engaged with the linear guide, and at least one magnet on the magnet holder, and wherein the magnet holder and the timing belt are connected or engaged; wherein the longitudinal movement structure comprises: a motor mounting plate; a lifting motor fixed on the motor mounting plate, wherein the lifting motor is configured to actuate the movement of the motion platform in a direction substantially perpendicular to the motor mounting plate and/or to the motion platform.

In a fourth embodiment, provided herein is a magnetic rack according to the first, second or third embodiment above, characterized in that the motion platform further comprise a lifting guide bushing, the motor mounting plate further comprises a lifting guide column, wherein the lifting guide bushing and the lifting guide column are configured to engage with each other to allow the movement of the motion platform in a direction substantially perpendicular to the motor mounting plate and/or to the motion platform.

In a fifth embodiment, provided herein is a magnetic rack according to any of the second, third, and fourth embodiments above, characterized in that the magnetic rack further comprise a photoelectric block column and a photoelectric sensor, wherein the photoelectric sensor is on the motor mounting plate, and the photoelectric block column is on the motion platform.

In a sixth embodiment, provided herein is a magnetic rack according to any of the first, third, fourth, and fifth embodiments above, characterized in that the magnetic rack further comprises a photoelectric block element (e.g., a photoelectric sheet) and a photoelectric limit element (e.g., a home photoelectric element), wherein the photoelectric block element is on the magnet holder, and the photoelectric limit element is on the motion platform and in proximity to the driven wheel.

In a seventh embodiment, provided herein is a magnetic rack according to any of the first, third, fourth, fifth, and sixth embodiments above, characterized in that the magnetic rack further comprises a fixing belt plate on the timing belt, wherein the fixing belt plate and the magnet holder are connected or engaged with each other.

In a eighth embodiment, provided herein is a magnetic rack according to any of the first to seventh embodiments above, characterized in that the magnetic rack further comprises a mounting seat and a tray for receiving one or more reaction tubes or plates, wherein the tray is configured to be placed on or in the mounting seat; wherein the motor mounting plate and/or the motion platform are optionally housed in the mounting seat.

In a ninth embodiment, provided herein is a magnetic rack according to any of the first and third to eighth embodiments above, characterized in that the magnetic rack further comprises a driven wheel bearing and a driven wheel bearing housing, wherein the driven wheel and the driven wheel bearing are connected or engaged with each other, the driven wheel bearing and the driven wheel bearing housing are connected or engaged with each other, and the driven wheel bearing housing is on the motion platform.

In one aspect, the magnetic rack disclosed herein comprises a lateral movement structure. In one embodiment, the lateral movement structure comprises a motion platform, which comprises a driving wheel and a driven wheel. In one aspect, one or both of the driving wheel and the driven wheel are mounted to the motion platform. The driving wheel and/or the driven wheel can be releasably mounted or permanently fixed to the motion platform. In one aspect, the driving wheel and the driven wheel are positioned at or near the ends of the motion platform. In one aspect, the driving wheel and the driven wheel are such positioned that a timing belt engaging both wheels is capable of moving in a direction from one end of the motion platform to another end. In certain embodiments, the magnetic rack further comprises a drive wheel motor. In one embodiment, the driving wheel and the drive wheel motor are connected or engaged with each other, and the driving wheel and the driven wheel are connected or engaged by a common structure, such as a timing belt. In some embodiments, the lateral movement structure further comprises a linear guide. The linear guide can be releasably mounted or permanently fixed to the motion platform. In one aspect, the linear guide is provided on or above the motion platform. In another aspect, at least one magnet holder is provided on the linear guide to engage with the linear guide. In some embodiments, the magnet holder holds at least one magnet. In one aspect, the magnet holder and the timing belt are coupled, such that the magnet holder is capable of moving along with the timing belt. The magnet holder can be releasably mounted or permanently fixed onto the timing belt.

In another aspect, the magnetic rack disclosed herein comprises a longitudinal movement structure. In certain embodiments, the magnetic rack comprises a lifting motor, for example, a lifting motor which actuates all or part of the longitudinal movement structure to move up or down along a fixed axis. In one aspect, the magnetic rack comprises a motor mounting plate and the lifting motor is releasably or permanently mounted on the motor mounting plate. In one aspect, the magnetic rack further comprise at least one magnet holder. In one aspect, the magnet holder is provided on a motion platform, which can be moved up or down by the lifting motor. In other aspects, at least one magnet is provided on the at least one magnet holder.

In another aspect, provided herein is a magnetic rack comprising a lateral movement structure and a longitudinal movement structure. In one embodiment, the lateral movement structure comprises a motion platform, and a driving wheel and a driven wheel. In one aspect, one or both of the driving wheel and the driven wheel are mounted to the motion platform. The driving wheel and/or the driven wheel can be releasably or permanently mounted to the motion platform. In one aspect, the driving wheel and the driven wheel are positioned at or near the ends of the motion platform. In one aspect, the driving wheel and the driven wheel are such positioned that a timing belt engaging both wheels is capable of moving in a direction from one end of the motion platform to another end. In certain embodiments, the driving wheel is actuated by a drive wheel motor, and the driving wheel is connected to or engaged with the drive wheel motor. In one aspect, the driving wheel and the driven wheel are connected or engaged by a common structure, such as a timing belt. In some aspects, the driving wheel and the driven wheel are engaged with a synchronization gear belt. In some embodiments, the lateral movement structure further comprises a linear guide. In one aspect, the linear guide is provided on or above the motion platform. In another aspect, at least one magnet holder is provided on the linear guide, or engages with the linear guide. In some embodiments, the magnet holder holds at least one magnet. In one aspect, the magnet holder and the timing belt are coupled, such that the magnet holder is capable of moving along with the timing belt. In one aspect, the longitudinal movement structure comprises a lifting motor, for example, a lifting motor which actuates all or part of the longitudinal movement structure to move up or down along a fixed axis. In one aspect, the longitudinal movement structure comprises a motor mounting plate and the lifting motor is releasably or permanently mounted on the motor mounting plate. In one aspect, the lifting motor is fixed on the motor mounting plate.

In any of the preceding embodiments, the magnetic rack can further comprise a lifting guide column and a lifting guide bushing. In one aspect, the lifting guide bushing is provided on the motion platform, e.g., the motion platform of the lateral movement structure, or engages with the motion platform, e.g., the motion platform of the lateral movement structure. In another aspect, the lifting guide column is provided on the motor mounting plate of the longitudinal movement structure, or engages with the motor mounting plate of the longitudinal movement structure. In particular embodiments, the lifting guide bushing and the lifting guide column are engaged, such that the motion platform of the lateral movement structure can move up and down smoothly.

In alternative embodiments, the lifting guide bushing is provided on the motor mounting plate of the longitudinal movement structure, or engages with the motor mounting plate of the longitudinal movement structure. In another aspect, the lifting guide column is provided on the motion platform, e.g., the motion platform of the lateral movement structure, or engages with the motion platform, e.g., the motion platform of the lateral movement structure. Thus, the lifting motor can be provided on the motion platform to actuate the longitudinal movement of the motion platform.

In one aspect, the magnetic rack provided herein further comprises one or more photoelectric sensors and/or one or more photoelectric block columns. In one embodiment, the photoelectric sensor is provided on the motor mounting plate of the longitudinal movement structure. In another embodiment, the photoelectric block column is provided on the motion platform, e.g., the motion platform of the lateral movement structure. In one aspect, the starting point or position of a longitudinal movement of the magnetic rack is set at a position where the photoelectric block column blocks or reduces a signal emitted from and/or detected by the photoelectric sensor.

In alternative embodiments, the photoelectric sensor is provided on the motion platform, e.g., the motion platform of the lateral movement structure. In another embodiment, the photoelectric block column is provided on the motor mounting plate of the longitudinal movement structure.

In one embodiment, the magnetic rack provided herein further comprises one or more photoelectric sheets (photoelectric block elements) and one or more home photoelectric elements (photoelectric limit elements or devices).

In some embodiments, the photoelectric block element is provided on the magnet holder. In other embodiments, the home photoelectric element is provided on the motion platform of the lateral movement structure. In one aspect, the starting point or position of a lateral movement of the magnetic rack is set at a position where the photoelectric block element blocks or reduces a signal emitted from and/or detected by the home photoelectric element or device.

In alternative embodiments, the photoelectric block element is provided on the motion platform of the lateral movement structure. In other embodiments, the home photoelectric element is provided on the magnet holder.

In any of the preceding embodiments, the magnetic rack can further comprise a fixing belt plate. In one aspect, the fixing belt plate engages the timing belt (or synchronization gear belt) and the magnet holder, such that the drive wheel motor can actuate a lateral movement of the magnet holder, for example, a horizontal movement substantially parallel to the surface of the motion platform of the lateral movement structure.

In one aspect, the magnetic rack further comprises a holder (e.g., a mounting seat) and a tray (e.g., a tube tray). In one embodiment, one or more trays can be securely placed on the holder. In one aspect, the tube tray can be fixed on the mounting seat or releasably engages with the mounting seat. For example, the tube tray can be snapped on the mounting seat. In some embodiments, the motor mounting plate or the motion platform or both can be housed partially or entirely inside the mounting seat. For example, the motion platform can be installed inside the mounting seat, and its longitudinal movement and the lateral movement of the magnets occur inside the mounting seat.

In any of the preceding embodiments, the magnetic rack can further comprise a driven wheel bearing and optionally, a driven wheel bearing housing. In one aspect, the driven wheel and the driven wheel bearing are connected to or engaged with each other. In another aspect, the driven wheel bearing and the driven wheel bearing housing are connected or engaged. In a further aspect, the driven wheel bearing housing is provided on the motion platform of the lateral movement structure.

In any of the preceding embodiments, the number and arrangement of the magnet holders can be designed and/or adjusted according to the shape and size of the test tubes and/or individual tubes or wells of a test plate. For example, the distance between adjacent slots for magnets on the magnet holder can be automatically or manually adjusted. In some embodiments, for racks with a fixed number and/or arrangement of magnet holders, the number and arrangement of magnets can nonetheless be adjusted. For example, a row of four reaction tubes are placed on the tube tray, and the magnet holder contains eight slots for magnets. In this example, four magnets can be placed in four of the eight slots, such that each magnet aligns with one of the four reaction tubes.

Typically, the magnetic force for attracting magnetic beads in a test tube is determined by the distance between the magnet and the tube wall, when using a magnetic rack comprising a longitudinal movement structure. In one embodiment, the magnetic rack comprises the same number of magnet holders with the number of reaction tubes in a row of a test plate, such that each magnet corresponds to one reaction tube in the row. In specific embodiments, the motion platform (and thus the magnets in the magnet holders) is raised from an initial position. The final position can be determined, and adjusted if necessary, according to the height or level of liquid in the reaction tube. In one aspect, the magnet is positioned close to the liquid level in the reaction tube in order to attract the magnetic beads in the reaction volume to the side wall of the tube as quickly as possible. In one aspect, the attraction of magnetic beads among reaction tubes in the row of the test plate is synchronized. Next, the magnets are lowered, for example, to a position close to the bottom portion of the side wall of the reaction tube. In one aspect, the magnetic beads stuck on the side wall are moved to the bottom of the test tubes, and the attraction process is completed.

When using a magnetic rack comprising a lateral movement structure, the magnetic force for attracting magnetic beads in a test tube typically is determined by the distance between the magnet and the tube wall. In some embodiments, at least one magnet is provided in the magnetic rack for each reaction tube in a row of a test plate. In specific embodiments, the magnet is first moved toward the side wall of the reaction tube along the linear guide, and the magnetic beads in the reaction volume are attracted onto the side wall of the tube, and the attraction process is completed. In one aspect, the attraction of magnetic beads among multiple reaction tubes in the row within the test plate is synchronized.

In some embodiments, a magnetic rack comprising both a lateral movement structure and a longitudinal movement structure is used as follows. Typically, the magnetic force for attracting magnetic beads in a reaction tube is determined by the distance between the magnet and the tube wall, for example, the tube wall of a well in a 96-well plate placed on the tube tray. In one aspect, the magnet is first raised from an initial position to a final position. The final position can be determined, and adjusted if necessary, according to the height or level of liquid in the reaction tube. In one aspect, the magnet is positioned close to the liquid level in the reaction tube in order to attract the magnetic beads in the reaction volume to the side wall of the tube as quickly as possible. Next, the magnets are lowered, for example, to a position close to the bottom portion of the side wall of the reaction tube, and the magnetic beads stuck on the side wall are moved to the bottom of the test tubes. Then, the magnets are moved laterally closer to the bottom of the reaction tube, for example, to a position right beneath the bottom of the reaction tube, in order to increase the magnetic attraction force. For example, the magnet holders can be moved horizontally (along the x-axis) along the linear guide and in parallel to the surface of the motion platform. The magnets can physically touch the bottom of the tube, or be at a distance of about 0.1 mm, about 0.5 mm, about 1 mm, or about 5 mm vertically from the bottom of the tube. After drawing the liquid of the reaction tube, the magnets are lowered longitudinally (along the y-axis) to the longitudinal initial position. In certain aspects, this position is different from the initial position of the magnets because the magnets have been moved horizontally, i.e., the two positions can share the same y-axis coordinate but have different x-axis coordinates. In one aspect, during the aspiration (the suction process), the magnetic beads are attached to the bottom of the tube by the magnetic force, facilitating the separation of liquid and the magnetic beads. In one embodiment, the aspired liquid is substantially free of the magnetic beads and/or molecules, complexes, viral particles, organelles, cellular components, or cells coupled to the magnetic beads. Then, one or more reagents are added to the reaction tube, for example, by pipetting using a clean pipette tip. In one embodiment, pipette mixing is performed in the absence of magnetic force, such that magnetic beads can be mixed thoroughly and uniformly with the reagents. In one aspect, mixing with beads in the bottom of the reaction tubes eliminates or reduces adsorption of the beads to the side wall. In another aspect, this process avoids the phenomenon that when the beads are adsorbed on the side wall, loss of liquid will increase the adhesion of the beads to the side wall, which is not conducive to pipette mixing.

After the reaction is completed, the magnets can again be moved horizontally, for example, to the next row of reaction tubes in the test plate (for example, below the next row of reaction tubes). The above process can be repeated for addition reactions (e.g., with additional reagents added to the reaction tubes) in the same reaction tubes, and/or repeated for the same reaction in a different row of reaction tubes, until a final product in obtained. Thus, magnetic adsorption/attraction and chemical/biological reactions among different reactions tubes can be synchronized in a batch format.

Typically, the present magnetic rack and methods of using the same disclosed herein offer one or more advantages. First, since the magnets can be moved up or down (vertical or longitudinal movement) to adjust the strength of magnetic forces, the present magnetic rack is compatible (or can be adjusted to be compatible) with magnetic beads from different manufacturers. In one aspect, the magnetic rack avoids clustering or aggregation of magnetic beads due to magnetic forces being too strong. In another aspect, the magnetic rack can achieve rapid attraction and adsorption of beads to the tube wall by controlling the speed of the moving magnets (horizontal movement and/or vertical movement), thereby facilitating separation of the magnetic beads and the sample or reaction liquid. Second, since the magnets can be moved laterally (e.g., horizontal movement), sample addition (e.g., by pipetting) and bead adsorption can be performed simultaneously, preferably by an automated process, leading to improved speed and/or efficiency of sample handling. Due to the synchronization of the reactions in different tubes, reproducibility and success rates of multiple reaction runs can be improved.

In certain embodiments, microbeads used herein are paramagnetic particles, whose magnetic dipoles are induced by externally applied magnetic fields and return to zero when external field is turned off. For such applications, commercially available paramagnetic or other magnetic particles may be used, for example, SPHERO™ Magnetic Particles (Spherotech, Inc.), MagneSil™ Paramagnetic Particles (silica-paramagnetic particles from Promega Corporation), or MagneSphere® Paramagnetic Particles (Promega Corporation). Many of these magnetic particles are between below micron (for example, 50 nm-0.5 micron) and tens of microns. They may have different structures and compositions. One type of magnetic particles has ferromagnetic materials encapsulated in thin latex, for example, polystyrene, and shells. Another type of magnetic particles has ferromagnetic nanoparticles diffused in and mixed with latex for example polystyrene, surroundings. The surfaces of both these particle types are polystyrene in nature and may be modified to link to various types of molecules.

Figure 1:
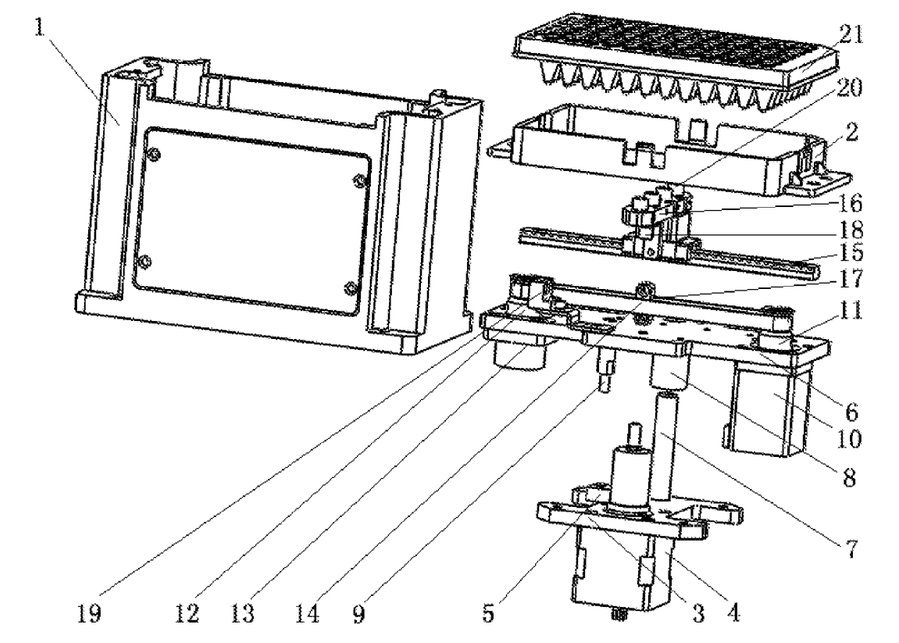

Turning to FIG. 1, a magnetic rack of the present disclosure is shown. The magnetic rack comprises a mounting seat (1) for a tube tray (2), a longitudinal movement structure, and a lateral movement structure. Tube tray 2 is placed on mounting seat 1. When the device is ready for use, a test plate (21), for example, a PCR microplate is placed on tube tray 2. Test plate 21 may contain multiple rows of reaction tubes, for example, a 96-well plate can have 12 rows, each with 8 reaction tubes. The longitudinal movement structure can include a lifting motor (4) and a lifting guide column (7). As shown in FIG. 1, lifting motor 4 and lifting guide column 7 can be fixed to a motor mounting plate (3). Motor mounting plate 3 can be fixed in mounting seat 1. Typically, motor mounting plate 3 is located below tube tray 2.

The lateral movement structure can include a motion platform (6), a driving wheel (11), a driven wheel (12), a drive wheel motor (10), a driven wheel bearing (not shown in FIG. 1), and a driven wheel bearing housing (13). Typically, driving wheel (11) and driven wheel (12) are each located at one end of motion platform 6. Drive wheel motor 10 and driving wheel 11 engage each other, or are connected directly or indirectly, such that the drive well motor can actuate the rotating movement of the driving well. Driven wheel 12 and the driven wheel bearing engage each other, or are connected directly or indirectly. The driven wheel bearing and driven wheel bearing housing 13 engage each other, or are connected directly or indirectly. As shown in FIG. 1, driven wheel bearing housing 13 can be located on motion platform 6, for example, on the same or different sides of motion platform 6 with driven wheel 12. Driving wheel 11 and driven wheel 12 are engaged with a timing belt (14). Timing belt 14 runs along (for example, inside) a linear guide (15) on motion platform 6. Driving wheel 11 actuates timing belt 14, which in turn actuates driven wheel 12. A magnet holder (16) is provided to engage with linear guide 15 and typically, magnet holder 16 can move or slide smoothly along linear guide 15. Magnet holder 16 and timing belt 14 engage each other, or are connected directly or indirectly by a fixing belt plate 17, such that time belt 14 actuates the movement of magnet holder 16 between the two ends of motion platform 6 and along linear guide 15. One or more magnets (20) can be provided on magnet holder 16. As shown in FIG. 1, the one or more magnets can be arranged on magnet holder 16 so that each magnet corresponds to a reaction tube of a row within test plate 21. When test place 21 is placed on tube tray 2, magnet holder 6 can be moved up or down and/or left to right, such that each magnet aligns with its corresponding reaction tube. The distance and relative position of each magnet to its corresponding reaction tube is the same or substantially identical among the multiple reaction tubes. This arrangement facilitates synchronization of reactions in different reaction tubes and batch processing of samples.

In FIG. 1, the magnetic rack further comprises a lifting guide bushing (8), located on motion platform 6. Typically, lifting guide bushing 8 engages a lifting guide column (7). In a typical magnetic rack, lifting guide column 7 is provided on motor mounting plate 3 and power is provided by lifting motor 4, in order to actuate motion platform 6 and its subsidiary structure to move up or down.

In FIG. 1, the magnetic rack further comprises a photoelectric sensor (5), for example, a U-typed EO sensor as shown in the FIGURE, and a photoelectric block column (9). Typically, photoelectric sensor 5 is provided on motor mounting plate 3, and photoelectric block column 9 is provided on motion platform 6, and the pair are used to set the initial position of motion platform 6 (e.g., relative to lifting motor 4) and determine and/or adjust the distance of its vertical movement (e.g., relative to lifting motor 4). In the example of a U-typed EO sensor as shown in FIG. 1, photoelectric block column 9 can move between the two arms of the U-typed EO sensor, and relative position between the photoelectric block column and the two arms can be used to set the initial vertical position, and/or determine and/or adjust the distance of the vertical movement.

The magnetic rack shown in FIG. 1 further comprises a photoelectric block sheet (18) and a home photoelectric element or device (19). Photoelectric block sheet 18 is typically on magnet holder 16 and moves with the magnet holder along linear guide 15, and home photoelectric device 19 is typically fixed on motion platform 6, for example, near driven wheel 12. The photoelectric block sheet and home photoelectric device are used to set the initial position of magnet holder 16 (e.g., relative to drive wheel motor 10) and determine and/or adjust the distance of its horizontal movement (e.g., relative to drive wheel motor 10).

Use of Magnetic Racks

A typical process using the magnetic rack shown in FIG. 1 is provided. Before or after test plate 21 is loaded on the magnetic rack in tube tray 2, an automatic pipetting station can be used to add one or more reagents, one or more samples, and/or magnetic beads to the first row of reaction tubes in the test plate. The magnetic beads can be pre-coupled with one or more reagents, molecules, or complexes. Alternatively, magnetic beads without pre-coupled reagents are added into the reaction tubes. As an example, the first row of a 96-well PCR microplate has 8 reaction tubes. For such a plate, 8 identical magnets can be provided in a magnet holder designed to present the magnets at equal distances to the reaction tube walls when the magnetic rack moves the magnet holder horizontally and/or vertically to or away from the row of reaction tubes.

As the reagent(s), sample, and/or magnetic beads react in the reaction tubes, magnets 20 are positioned to the lower left of PCR microplate 21, for example, magnets 20 are positioned below and to the left of the leftmost row of reaction tubes within PCR microplate 21. At this time, drive wheel motor 10 is at a "home location", for example, a "0" point position in the horizontal direction of movement when photoelectric block sheet 18 blocks home photoelectric device 19. At the same time, lifting motor 4 is also at a "home location," for example, a "0" point position in the vertical direction of movement when photoelectric block column 9 blocks U-typed EO sensor 5.

After the reagent reaction is completed, drive wheel motor 10 is rotated according to a set program, and timing belt 14 and magnet holder 16 (connected by fixing belt plate 17) are actuated. At this time, the portion of timing belt 14 near driven wheel 12 and driven wheel bearing housing 13 is in tension, and timing belt 14 is thus actuated to move magnets 20 (on magnet holder 16) along the direction of linear guide 15. The magnets are moved (horizontally to the right) to below the middle of the first row and the second row of PCR microplate 21. Then, lifting motor 4 is actuated to move motion platform 6 and related parts (including magnets 20 on magnet holder 16) along the direction of lifting guide column 7 and lifting guide bushing 8. The magnets are moved up to a position at or near the liquid level of the PCR microplate, and magnetic forces act on the magnetic beads in the first row of reaction tubes. Typically, magnetic forces can be adjusted according to the magnetism of the beads and the liquid levels in the reaction tubes, and the adjustment can be automated. Magnetic forces of permanent magnet acting on the beads can be associated with the distance between the magnet and the beads, the adsorption time, and motion damping of the beads in different liquids. Typically, one or more of these factors are taken into consideration when adjusting the magnetic forces.

At the beginning of magnetic attraction (e.g., adsorption of magnetic beads onto the wall of a reaction tube), suspended microbeads are adsorbed onto one side of the wall near the magnet, i.e., in this example to the right side walls of the first row of reaction tubes. Then, lifting motor 4 is actuated to move motion platform 6 and related parts along the direction of lifting guide column 7 and lifting guide bushing 8. The magnet holders and magnets in the holders are moved down to a position near the bottom of PCR microplate 21. In specific examples, drive wheel motor 10 is then actuated to move motion platform 6 (and thus the magnet holders and magnets) horizontally to the left, e.g., to a position horizontally closer to the first row. In other examples, motion platform 6 can be moved in the vertical direction as it is being moved in the horizontal direction, to a position horizontally closer to the bottom of the first row of reaction tubes. At this position, the beads are adsorbed to the bottom of the reaction tubes as small clusters, and mobility of the magnetic beads are minimized. Then, the workstation is configured to automatically aspirate the liquid (e.g., waste that does not contain magnetic beads coupled to one or more target molecules of interest) using clean disposable pipette tips. The magnetic beads are immobilized by magnetic forces, and typically are not disturbed or released into the solution even when the solution is being aspired.

Next, lifting motor 4 is actuated to move the magnets down to the "Home location," to increase the distance between magnetic beads and the magnets. In some examples, the increase in distance is sufficient to release the magnetic beads from the magnetic forces exerted by the magnets, for example, permanent magnets. In other examples, the magnets can comprise ferromagnetic materials. In yet other examples, the magnets can be electromagnets, whose magnetic fields are proportional to the number of loops of wire, to the cross-section of each loop, and to the current passing through the wire. Thus, the magnetic forces exerted on the beads can be adjusted without moving the electromagnet relative to the beads, for example, by altering the current passing through the coil of wire of electromagnets. By releasing the magnetic beads from the magnetic forces exerted by the magnets, additional reagents can be added into the reaction tubes, easily and uniformly mixed with the beads, and thoroughly reacted with reagents and/or target molecules coupled to the beads. In particular embodiments, multiple washing and/or reaction steps can be performed in tandem in the same reaction tubes.

In choosing magnets 20, typically very strong magnetic forces between the magnets and magnetic beads should be avoided. Otherwise, when the magnetic beads are moved away from the magnets and/or released from the magnetic forces, residual magnetism among the magnetic beads can cause the beads to cluster, making it difficult to disperse the beads for thorough mixing.

The above illustrates a complete process for magnetic adsorption in the first row of reaction tubes of PCR microplate 21, according to some embodiments. In other embodiments, odd-numbered rows of the test plate are used as reaction tubes, such that magnetic adsorption in the third row does not affect beads in the first row. In this example, the position of magnets 20 in the horizontal direction is in the middle of the third and fourth rows of PCR microplate 21. The same process can be repeated to perform reactions in the fifth, seventh, ninth, and eleventh rows of the 96-well plate, for example, by using an automatic liquid workstation, in order to prepare or process 48 samples (6 rows with each row having 8 reaction tubes). In particular embodiments, single-stranded DNA is prepared from the 48 samples using a process disclosed herein.

In yet other embodiments, rows of reaction tubes are spaced from each other such that performing magnetic adsorption in one row does not affect the beads in an immediately adjacent row.

In particular embodiments, the test plate can be in the form of a microarray chip. A microarray chip can include any solid substrate with a plurality of one-, two- or three-dimensional micro structures or micro-scale structures on which certain processes, such as physical, chemical, biological, biophysical or biochemical processes, etc., can be carried out. The micro structures or micro-scale structures such as, channels and wells, are incorporated into, fabricated on or otherwise attached to the substrate for facilitating physical, biophysical, biological, biochemical, chemical reactions or processes on the chip. The chip may be thin in one dimension and may have various shapes in other dimensions, for example, a rectangle, a circle, an ellipse, or other irregular shapes. The size of the major surface of chips can vary considerably, e.g., from about 1 $mm^2$ to about 0.25 $m^2$. Preferably, the size of the chips is from about 4 $mm^2$ to about 25 $cm^2$ with a characteristic dimension from about 1 mm to about 5 cm. The chip surfaces may be flat, or not flat. The chips with non-flat surfaces may include channels or wells fabricated on the surfaces. In particular embodiments, microbeads are provided in a microarray chip (for example, in the wells of a microarray chip), and magnets are provided in a magnetic rack disclosed herein for interaction with the microbeads. In certain aspects, micromagnets can be used to match the size of each channel or well of the microarray chip. Sample preparation and/or reaction can be performed in the channels or wells.

The present magnetic rack can be used to process or detect a target in a sample, e.g., a cell, a cellular organelle, a virus, a molecule and an aggregate or complex thereof. For example, nucleic acid can be extracted and/or purified from a cell. Exemplary cells include animal cells, plant cells, fungus cells, bacterium cells, recombinant cells and cultured cells. Animal, plant, fungus, bacterium cells can be derived from any genus or subgenus of the Animalia, Plantae, fungus or bacterium kingdom. Cells derived from any genus or subgenus of ciliates, cellular slime molds, flagellates and microsporidia can also be assayed and/or processed by the present methods. Cells derived from birds such as chickens, vertebrates such as fish and mammals such as mice, rats, rabbits, cats, dogs, pigs, cows, ox, sheep, goats, horses, monkeys and other non-human primates, and humans can be assayed and/or processed by the present methods.

For animal cells, cells derived from a particular tissue or organ can be assayed and/or processed using a device disclosed herein. For example, connective, epithelium, muscle or nerve tissue cells can be assayed and/or processed. Similarly, cells derived from an internal animal organ such as brain, lung, liver, spleen, bone marrow, thymus, heart, lymph, blood, bone, cartilage, pancreas, kidney, gall bladder, stomach, intestine, testis, ovary, uterus, rectum, nervous system, gland, internal blood vessels, etc. can be assayed and/or processed. Further, cells derived from any plants, fungi such as yeasts, bacteria such as eubacteria or archaebacteria can be assayed and/or processed. Recombinant cells derived from any eucaryotic or prokaryotic sources such as animal, plant, fungus or bacterium cells can also be assayed and/or processed. Body fluid such as blood, urine, saliva, bone marrow, sperm or other ascitic fluids, and subfractions thereof, e.g., serum or plasma, can also be assayed and/or processed using a magnetic rack of the present disclosure.

Exemplary cellular organelles include nuclei, mitochondria, chloroplasts, ribosomes, ERs, Golgi apparatuses, lysosomes, proteasomes, secretory vesicles, vacuoles and microsomes. Exemplary molecules include inorganic molecules, organic molecules and a complex thereof. Exemplary organic molecules include amino acids, peptides, proteins, nucleosides, nucleotides, oligonucleotides, nucleic acids, vitamins, monosaccharides, oligosaccharides, carbohydrates, lipids and a complex thereof. Any proteins or peptides can be assayed and/or processed as disclosed herein. For example, enzymes, transport proteins such as ion channels and pumps, nutrient or storage proteins, contractile or motile proteins such as actins and myosins, structural proteins, defense protein or regulatory proteins such as antibodies, hormones and growth factors can be assayed and/or processed. Proteineous or peptidic antigens can also be assayed and/or processed using a device disclosed herein.

Nucleic acids, including single-, double and triple-stranded nucleic acids, can be assayed and/or processed using a magnetic rack of the present disclosure. Examples of such nucleic acids include DNA, such as A-, B- or Z-form DNA, and RNA such as mRNA, miRNA, piRNA, tRNA and rRNA.

The presently disclosed magnetic rack and method of using the same are compatible with existing techniques for nucleic acid extraction. Methods of extracting nucleic acids from cells are well known to those skilled in the art. A cell wall can be weakened by a variety of methods, permitting the nucleic acids to extrude from the cell and permitting its further purification and analysis. The specific method of nucleic acid extraction is dependent on the type of nucleic acid to be isolated, the type of cell, and the specific application used to analyze the nucleic acid. Many methods of isolating DNA are known to those skilled in the art, see for example the general reference Sambrook and Russell, 2001, "Molecular Cloning: A Laboratory Manual". For example, there are examples of chemically-impregnated and dehydrated solid-substrates for the extraction and isolation of DNA from bodily fluids that employ lytic salts and detergents and which contain additional reagents for long-term storage of DNA samples e.g. U.S. Pat. No. 5,807,527 detailing FTA paper, and U.S. Pat. No. 6,168,922 detailing Isocard Paper. There are also examples of particle separation methods, e.g. U.S. RE 37,891. A nucleic acid preparation using an existing extraction technique can be further extracted and/or purified using a magnetic rack disclosed herein.

Methods of isolating RNA, particularly messenger RNA (mRNA) are well known to those skilled in the art. Typically, cell disruption is performed in the presence of strong protein denaturing solutions, which inactivate RNAses during the RNA isolation procedure. RNA is then isolated using differential ethanol precipitation with centrifugation. As is well known, RNA is extremely labile and is sensitive to alkaline conditions, as well as RNAses, which degrade RNA. RNAses are ubiquitous within the environment and it has been found that they are difficult to remove from solutions and containers used to isolate RNA. Thus, in one embodiment, a magnetic rack disclosed herein and its components are RNAse-free, and are suitable for extraction and/or purification of RNA from a sample.

The invention claimed is:

1. A magnetic rack comprising a lateral movement structure and a longitudinal movement structure, wherein:
  (1) the lateral movement structure comprises:
    a motion platform;
    a driving wheel and a driven wheel on the motion platform;
    a drive wheel motor connected to the driving wheel;
    a timing belt engaging both the driving wheel and the driven wheel; and
    a magnet holder engaging the timing belt, which magnet holder is configured to hold one or more magnets,
    wherein the timing belt is configured to be actuated by the drive wheel motor and driving wheel to move the magnet holder laterally along a path on the motion platform:
  (2) the longitudinal movement structure comprises:
    a motor mounting plate;
    a lifting motor;
    a lifting guide bushing; and
    a lifting guide column;
    wherein the lifting guide bushing is connected to the motion platform and the lifting guide column is connected to the motor mounting plate,
    wherein the lifting guide bushing and the lifting guide column are configured to engage each other to form a lifting structure, and
    wherein the lifting motor is configured to actuate the lifting structure to move the motion platform in a direction substantially perpendicular to the motion platform.

2. The magnetic rack of claim 1, further comprising a photoelectric block on the motion platform.

3. The magnetic rack of claim 1, wherein the motor mounting plate comprises a photoelectric sensor.

4. The magnetic rack of claim 1, further comprising a photoelectric block element on the magnet holder and a photoelectric limit element on the motion platform.

5. The magnetic rack of claim 1, further comprising a fixing belt plate on the timing belt,
  wherein the fixing belt plate and the magnet holder are connected or engage each other, and wherein the timing belt actuates the lateral movement of the magnet holder via the fixing belt plate.

6. The magnetic rack of claim 1, further comprising a mounting seat and a tray for receiving one or more reaction tubes or plates, wherein the tray is configured to be placed on or in the mounting seat.

7. The magnetic rack of claim 6, wherein the mounting seat houses the lateral movement structure and the longitudinal movement structure.

8. The magnetic rack of claim 1, further comprising a driven wheel bearing housing on the motion platform.

9. The magnetic rack of claim 1, wherein the lateral movement structure further comprises a linear guide on the motion platform, wherein the magnet holder is connected to or engages the linear guide, and the timing belt is configured to move the magnet holder laterally along the linear guide.

10. The magnetic rack of claim 1, further comprising a photoelectric block element on the magnet holder.

11. The magnetic rack of claim 1, further comprising a photoelectric limit element on the motion platform.

12. The magnetic rack of claim 1, further comprising a mounting seat that houses the lateral movement structure.

13. The magnetic rack of claim 1, further comprising a mounting seat that houses the longitudinal movement structure.

14. The magnetic rack of claim 1, further comprising a tray for receiving one or more reaction tubes or plates, wherein the tray is configured to be placed on or in a mounting seat housing the lateral movement structure or the longitudinal movement structure.

15. A method of performing a magnetic bead-based process, comprising:
- placing a receptacle on the magnetic rack of claim 1, wherein the receptacle contains a sample with a magnetic bead;
- actuating the lifting motor of the longitudinal movement structure to move the motion platform comprising one or more magnets in the magnetic holder in a direction substantially perpendicular to the motion platform, whereby the one or more magnets are moved toward the receptacle to attract the magnetic bead onto a side wall of the receptacle; and
- actuating the drive wheel motor and driving wheel of the lateral movement structure to move the magnet holder laterally along a path on the motion platform, whereby the one or more magnets are moved toward the bottom of the receptacle to attract the magnetic bead from the side wall onto the bottom of the receptacle.

16. The method of claim 15, further comprising:
- a step of removing or adding a reagent or solution into the receptacle, wherein the magnetic bead remains adsorbed on the side wall of the receptacle when the reagent or solution is being removed or added, and
- a step of removing or adding a reagent or solution into the receptacle, wherein the magnetic bead remains adsorbed on the bottom of the receptacle when the reagent or solution is being removed or added.

17. The method of claim 15, further comprising:
- a step of actuating the lifting motor to move the motion platform substantially perpendicular to the motion platform, whereby the one or more magnets are moved away from the receptacle to release the magnetic bead from the side wall of the receptacle; and
- a step of actuating the drive wheel motor and driving wheel to move the magnet holder laterally on the motion platform, whereby the one or more magnets are moved away from the receptacle to release the magnetic bead from the bottom of the receptacle.

18. The method of claim 15, further comprising:
- a step of removing or adding a reagent or solution into the receptacle, wherein the magnetic bead remains adsorbed on the side wall of the receptacle when the reagent or solution is being removed or added.

19. The method of claim 15, further comprising:
- a step of removing or adding a reagent or solution into the receptacle, wherein the magnetic bead remains adsorbed on the bottom of the receptacle when the reagent or solution is being removed or added.

20. The method of claim 15, further comprising:
- a step of actuating the lifting motor to move the motion platform substantially perpendicular to the motion platform, whereby the one or more magnets are moved away from the receptacle to release the magnetic bead from the side wall of the receptacle.

21. The method of claim 15, further comprising:
- a step of actuating the drive wheel motor and driving wheel to move the magnet holder laterally on the motion platform, whereby the one or more magnets are moved away from the receptacle to release the magnetic bead from the bottom of the receptacle.

* * * * *